United States Patent

Numata et al.

[11] 4,012,379
[45] Mar. 15, 1977

[54] 7-ACETOACETAMIDOCEPHEM COMPOUNDS

[75] Inventors: Mitsuo Numata, Takatsuki; Masayoshi Yamaoka, Osaka; Yoshio Imashiro, Nishinomiya; Isao Minamida, Kyoto, all of Japan

[73] Assignee: Takeda Chemical Industries, Ltd., Japan

[22] Filed: Oct. 15, 1974

[21] Appl. No.: 514,991

[30] Foreign Application Priority Data

Oct. 15, 1973 Japan .............................. 48-115449

[52] U.S. Cl. .............................. 260/243 C; 424/246
[51] Int. Cl.² ...................................... C07D 501/36
[58] Field of Search ............................... 260/243 C

[56] References Cited

UNITED STATES PATENTS 3,557,104 1/1971 Bickel et al. .................. 260/243 C
3,864,340 2/1975 Ishimaru et al. ............... 260/243 C

FOREIGN PATENTS OR APPLICATIONS 42-8877 4/1967 Japan .............................. 260/243 C Primary Examiner—Paul M. Coughlan, Jr.
Attorney, Agent, or Firm—Craig & Antonelli

[57] ABSTRACT

Novel compounds of the formula:

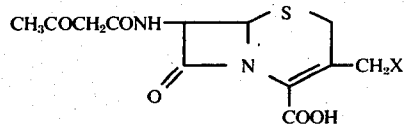

wherein X is a lower alkanoyloxy group or a substituted thio group, where the substituent is a nitrogen-containing heterocyclic group, or a pharmaceutically acceptable salt or ester thereof, have a broad antimicrobial spectrum, and besides they are readily absorbed into the living body. Thus, the compounds are useful as therapeutic agent for various bacterial infections of animals including human beings.

18 Claims, No Drawings

7-ACETOACETAMIDOCEPHEM COMPOUNDS

The present invention relates to novel and useful 7-acetoacetamidocephem compounds and to a method for preparing them, and more particularly to compounds of the formula:

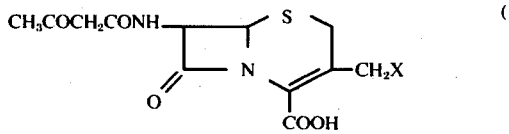

wherein X is a lower alkanoyloxy group or a substituted thio group, where the substituent is nitrogen-containing heterocyclic group, or a pharmaceutically acceptable salt or ester thereof.

Heretofore, as acylating agents for the 7-amino groups of 7-aminocephalosporanic acid compounds, there have been employed the acid anhydrides and acid halides of carboxylic acids. It follows, then, that to obtain cephalosporin derivatives having an acetoacetamido group in 7-position, there must be available the acid anhydride or acid halide of acetoacetic acid. However, acetoacetic acid is so much of an unstable compound that its acid anhydride and halide cannot be synthesized.

The present inventors discovered that by reacting a 7-aminocephalosporanic acid derivative of the formula:

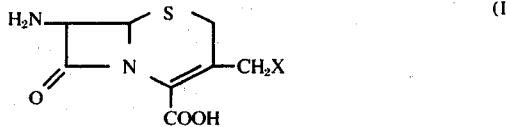

(wherein X is as hereinbefore defined) with diketene, the 7-amino group of 7-aminocephalosporanic acid derivative (II) can be easily acetoacetylated without inducing side reactions such as a fission of the β-lactam ring and a shift of the Δ³-double bond; that when the 3-position of the resulting 7-acetoacetamidocephalosporanic acid derivative (I) is a lower alkanoyloxymethyl group, this particular position can be converted to a nitrogen-containing heterocyclic ring-thiomethyl group by reacting (I) with a thiol compound of the formula:

(wherein R is a nitrogen-containing heterocyclic group); and that the resulting contempleted compound 7-acetoacetamidocephem compound (I), because of its prominent antimicrobial activity as well as the readiness with which it is absorbed into the body, can be used as a therapeutic agent in the treatment of various infections in animals including human beings. This invention has been conceived and developed on the basis of the above findings.

It is the principal object of the present invention to provide the novel and useful compound (I).

Another object of the present invention is to provide a method for producing compound (I).

A further object is to provide new pharmaceutical compositions containing compound (I).

Other objects of the present invention and advantageous features thereof will become apparent as the description proceeds.

In the formulas given hereinbefore, X stands for a lower alkanoyloxy group such as acetoxy or propionyloxy, or a substituted thio group where the substituent is a nitrogen-containing heterocyclic group. The nitrogen-containing heterocyclic group contains at least one nitrogen atom which may be in the oxide form, which heterocyclic group may contain, in addition to said nitrogen atom or atoms, such other hetero atoms as oxygen and sulfur. The typical nitrogen-containing heterocyclic group may be exemplified by five- or six-membered rings, e.g., pyridine, N-oxidopyridine, pyrimidine, pyridazine, N-oxidopyridazine, pyrazole, imidazole, thiazole, 1,2,3-thiadiazole, 1,2,4-thiadiazole, 1,3,4-thiadiazole, 1,2,5-thiadiazole, 1,2,3-oxadiazole, 1,2,4-oxadiazole, 1,3,4-oxadiazole, 1,2,5-oxadiazole, 1,2,3-triazole, 1,2,4-triazole, 1H-tetrazole, 2H-tetrazole, etc. These five- or six-membered rings may be substituted by one or more substituents selected from the groups consisting of lower alkyls such as methyl, ethyl, propyl, isopropyl, butyl, isobutyl, etc., lower alkoxyls such as methoxy, ethoxy, propoxy, isopropoxy, butoxy, etc., halogens such as chlorine, bromine, iodine, etc., substituted lower alkyls such as carboxymethyl, carbamoylmethyl, loweralkoxycarbonylmethyl (e.g., methoxycarbonylmethyl, ethoxycarbonylmethyl), N-loweralkylcarbamoylmethyl (e.g., N,N-dimethylcarbamoylmethyl), loweralkylthiomethyl (e.g., methylthiomethyl, ethylthiomethyl), N-loweralkylaminomethyl (e.g., N-ethylaminomethyl, N,N-dimethylaminomethyl), morpholinomethyl, etc., amino, N-substituted aminos such as sulfoalkylamino (e.g., 2-sulfoethylamino), [acylamino (e.g., acetylamino, propionylamino),] N-loweralkylaminomethylcarbonylamino (e.g., N-ethylaminomethylcarbonylamino, N,N-dimethylaminomethylcarbonylamino), etc., mercapto, alkylthio such as methylthio, ethylthio, etc., substituted alkylthio such as hydroxyethylthio, loweralkylcarbonyloxyethylthio (e.g., 2-isopropylcarbonyloxyethylthio), carboxymethylthio, loweralkoxycarbonylmethylthio (e.g., methoxycarbonylmethylthio, ethoxycarbonylmethylthio), N-loweralkylaminocarbonylmethylthio (e.g., N,N-dimethylaminocarbonylmethylthio, N,N-diethylaminocarbonylmethylthio), morpholinocarbonylmethylthio, N-loweralkylaminoethylthio (e.g., N-ethylaminoethylthio, N,N-dimethylaminoethylthio), sulfoalkylthio (e.g., 2-sulfoethylthio), loweralkoxymethylthio (e.g., methoxymethylthio, ethoxymethylthio), etc. and heterocyclic group such as morpholino, etc. to name but a few. More particularly, use can thus be made of nitrogen-containing heterocyclic groups substituted, for example, by 5-methyl-1,3,4-thiadiazolyl, 5-methyl-1,3,4-oxadiazolyl, 1-methyltetrazolyl, 6-methyl-1-oxidopyridazinyl, 3-methoxy-1-oxidopyridazinyl, 3-ethoxy-1-oxidopyridazinyl, 3-chloro-1-oxidopyridazinyl, etc., 5-morpholinomethyl-1,3,4-thiadiazolyl, 5-(N,N-dimethylcarbamoyl)methyl-1,3,4-thiadiazolyl, 5-carboxylmethyl-1,3,4-thiadiazolyl, 5-carbamoylmethyl-1,3,4-thiadiazolyl, 5-methoxycarbonylmethyl-1,3,4-thiadiazolyl, 5-methylthiomethyl-1,3,4-thiadiazolyl, 5-amino-1,3,4-thiadiazolyl, 5-acetylamino-1,3,4-thiadiazolyl, 5-(N,N-dimethylaminomethylcarbonyl)amino-1,3,4-thiadiazolyl, 5-mercapto-1,3,4-thiadiazolyl, 5-methylthio-1,3,4-thiadiazolyl, 5-(2-hydroxyethyl)thio-1,3,4-thiadiazolyl, 5-(2-isopropylcarbonyloxyethyl)thio-1,3,4-thiadiazolyl, 5-carboxymethylthio-1,3,4-thiadiazolyl, 5-ethoxycarbonylmethylthio-1,3,4-thiadiazolyl, 5-methoxycarbonylmethylthio-1,3,4-thiadiazolyl, 5-(N,N-dimethylaminocarbonylmethyl)thio-1,3,4-thiadiazolyl, 5-morpholinocarbonylmethylthio-1,3,4-thiadiazolyl, 5-(2-N,N-dimethylaminoethyl)thio-1,3,4-thiadiazolyl, 5-methoxymethylthio-1,3,4-thiadiazolyl, 1-(2-N,N-dimethylamino)ethyl-tetrazolyl, 1-carboxymethyltetrazolyl, 1-carbamoylmethyltetrazolyl, 1-methoxycarbonylmethyl-tetrazolyl, etc.

In the method of this invention, a 7-aminocephalosporanic acid derivative (II) is reacted with diketene. The 7-aminocephalosporanic acid derivative (II) is subjected to the reaction as the free acid or, alternatively, as a salt or easily cleavable ester thereof. As said salt, there may be mentioned, among others, the corresponding salts of alkali or alkaline earth metals or of organic amines, such as sodium, potassium, magnesium, calcium, aluminum, trimethylamine, triethylamine, tributylamine, etc. As said easily cleavable ester, there may be mentioned, among others, the reaction products with silylating agents such as trialkylhalogenosilanes, triaralkylhalogenosilanes, trialkoxyhalogenosilanes, hexaalkyldisilazanes, N, O-bis(trimethylsilyl) acetamide, etc.; silenating agents such as dialkyldihalogenosilanes, diaralkyldihalogenosilanes, etc.; tin-esterifying agents such as tin oxide(trialkyl tin), N-trialkylstannyldialkylamines, trialkylstannylalkoxides, etc.; alkylsulfonylalkyl halides; alkylthioalkyl halides; etc. When such an easily cleavable ester is used, it is necessary, after the reaction, to cleave the ester linkage in the routine manner.

The reaction is preferably conducted in a solvent. As said solvent, there may be mentioned acetone, dioxane, acetonitrile, chloroform, ethylene chloride, tetrahydrofuran, ethyl acetate, dimethylformamide, dimethylacetamide, pyridine and other common organic solvents which do not interfere with the reaction. Of these solvents, hydrophilic solvents can be used in admixture with water.

There is no particular limitation upon the reaction temperature but it is ordinarily preferably to carry out the reaction under cooling or at room temperature. While the reaction generally proceeds fast, a reaction time of not less than 30 minutes is required in many cases to obtain the contemplated product in satisfactory yield. The 7-acetoacetamidocephem compound (I) thus obtained can be collected and purified by known procedures such as solvent extraction, pH adjustment, phasic transfer, distillation, crystallization, recrystallization, chromatography, etc.

When the above method gives rise to a 7-acetoacetamido-3-loweralkanoyloxymethyl-3-cephem-4-carboxylic acid (hereinafter referred to briefly as 7-AAC), this compound can be further reacted with a thiol (III) to obtain a 7-acetoacetamidocephem compound of the general formula:

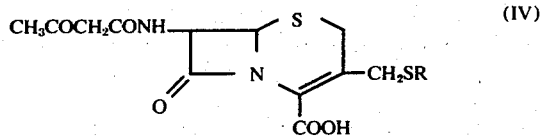

(IV)

(wherein R is as hereinbefore defined).

The 7-AAC to be used here may be an isolated pure product or the reaction mixture in which it is contained. The isolated 7-AAC is subjected to the reaction as the free acid or, as hereinbefore mentioned in connection with 7-aminocephalosporanic acid derivative (II), in the form of a salt or other compounds.

The thiol (III), too, is subjected to the reaction in the free form or in some other form such as one corresponding to (III) whose mercapto hydrogen has been replaced, for example, by an alkali metal, e.g. sodium, potassium or the like. Ordinarily this reaction is preferably conducted in a solvent. As said solvent, there may be mentioned, among others, acetone, chloroform, tetrahydrofuran, dimethylformamide, dimethylacetamide, methanol, ethanol, dimethylsulfoxide and other common organic solvents which do not interfere with the contemplated reaction, as well as water, although highly polar solvents are more desirable. Of these solvents, hydrophilic species can be used in combination with water. Usually this reaction is preferably carried out in the neighborhood of neutral pH.

And when 7-AAC and the thiol (III) in the free form is employed, the reaction may be maintained a pH of its mixture near neutral in the presence of a base such as an alkali metal hydroxide, e.g. sodium hydroxide, potassium hydroxide or the like; an alkali metal carbonate, e.g. sodium carbonate, potassium carbonate or the like; an alkali metal hydrogen carbonate, e.g. sodium hydrogen carbonate or the like; or a trialkylamine, e.g. trimethylamine, triethylamine, tripropylamine or the like. While there is no particular limitation upon the reaction temperature, the reaction usually is desirably carried out at room temperature.

To control the reaction velocity, the reaction may also be carried out under heating or cooling. The reaction time and other conditions of reaction should be selected with reference to the particular starting materials used and solvent, the reaction temperature, etc. The resultant 7-acetoacetamidocephem compound (IV) can be recovered and purified by conventional procedures similar to those hereinbefore mentioned.

The 7-acetoacetamidocephem compound (I) obtained by the foregoing method of this invention may be used with its carboxyl group in 4-position being free but may also be put to use with said carboxyl function having been previously converted to a salt, for example, by use of a nontoxic cation, e.g. sodium, potassium or the like; a basic amino acid, e.g. arginine, ornithine, lysine, histidine or the like; or a polyhydroxylalkylamine, e.g. N-methylglucamine, diethanolamine, triethanolamine, tris-hydroxymethylaminomethane or the like. It is also possible to esterify the 4-carboxyl function of the compound to produce biologically active ester derivatives that provide elevated blood levels and prolonged action.

The ester residues useful for this purpose are α-alkoxy-α-substituted methyl groups such as alkoxymethyl, α-alkoxyethyl or the like, for example, methoxymethyl, ethoxymethyl, isopropoxymethyl, α-methoxyethyl, α-ethoxyethyl, etc.; alkylthiomethyl groups such as methylthiomethyl, ethylthiomethyl, isopropylthiomethyl, etc.; and acyloxymethyl groups or α-acyloxy-α-substituted methyl groups such as pivaloyloxymethyl, α-acetoxybutyl, etc., to name but a few.

REFERENCE EXAMPLE

7-Acetoacetamido-3-(5-methyl-1,3,4-thiadiazol-2-yl) thiomethyl-3-cephem-4-carboxylic acid, 7-acetamido-3-(1-methyltetrazol-5-yl)thiomethyl-3-cephem-4-carboxylic acid and 7-acetoacetamido-3-(6-methyl-1-oxidopyridazin-3-yl)thiomethyl-3-cephem-4-carboxylic acid, all of which are among the contemplated compounds (I) of this invention, were found to be substantially as active as 7-(2-thienyl)acetoamido-3-acetoxymethyl-3-cephem-4-carboxylic acid (cephalothin) in in vitro assays against Escherichia coli NIHJ, Escherichia coli 0-111 and other pathogenic microorganisms. However, in therapeutic tests involving the parenteral administration of test compounds to mice infected with E. coli 0-111, the contemplated compounds of this invention had to be used in smaller doses to achieve the same effect as that attainable by use of cephalothin which is a known compound. Thus, whereas the minimum effective dose ($ED_{50}$) of cephalothin was 38.8 mg./kg., the $ED_{50}$ of 7-acetoacetamido-3- (5-methyl-1,3,4-thiadiazol-2-yl)thiomethyl-3-cephem-4-carboxylic acid was 6.22 mg./kg.; the $ED_{50}$ of 7-acetoacetamido-3-(1-methyltetrazol-5-yl)thiomethyl-3-cephem-4-carboxylic acid was 5.97 mg./kg.; and the $ED_{50}$ of 7-acetoacetamido-3-(6-methyl-1-oxidopyridazin-3-yl)thiomethyl-3-cephem-4-carboxylic acid was 7.69 mg./kg.

The 7-acetoacetamidocephem compounds (I) thus obtained have a broad antimicrobial spectrum, being active against gram-negative and gram-positive bacteria, besides the advantage that they are more readily absorbed into the living body than are the hitherto-known cephalosporins. Therefore, these compounds achieve antimicrobial effects in smaller amounts. Like the conventional cephalosporin preparations, the contemplated compounds (I) of this invention can be administered to the animals including human beings suffering from various microbial infections in the form of powders or, in combination with a physiologically acceptable vehicle or excipient, as solutions or suspensions according to the routine pharmaceutical practice.

When 7-acetoacetamido-3-(5-methyl-1,3,4-thiadiazol-2-yl)thiomethyl-3-cephem-4-carboxylic acid, 7-acetoacetamido-3-(1-methyltetrazol-5-yl)thiomethyl-3-cephem-4-carboxylic acid or 7-acetoacetamido-3-(6-methyl-1-oxide-pyridazin-3-yl)thiomethyl-3-cephem-4-carboxylic acid, for instance, is used for the treatment of infectious diseases in man, it is desirably administered parenterally at the daily dosage of about 5 to 200 milligrams per kg. body weight in 3 to 4 divided doses per day.

The NMR spectra in the examples to be given hereinafter were obtained using a spectrometer Varian T-60 or HR-100. The chemical shifts were expressed in parts per million (p.p.m.) relative to internal tetramethylsilane ($\delta$). Unless otherwise specified, deuteriochloroform was used as the solvent. The symbol s signifies a singlet, d a doublet, dd a double doublet, t a triplet, q a quartet, ABq a AB type quartet, m a miltiplet and J a coupling constant in Herz.

It is to be understood that the following examples are solely for the purpose of illustration and not to be construed as limitations of this invention, and that many variations may be resorted to without departing from the spirit and scope of this invention. In this specification, "g.", "mg.", "kg.", "ml.", "m.p.", "decomp." and "calcd.", are "gram", "milligram", "kilogram", "milliliter", "melting point", "decomposed" and "calculated", respectively. Further, "DMSO" means dimethylsulfoxide, "nm" nano meter, "$ED_{50}$" effective dose to 50% of animals tested, "IR" significant absorption bands in infrared spectrum and "UV" absorption in ultraviolet absorption spectrum, respectively. Resins named "Amberlite" are manufactured products by Rohm & Haas Co. in U.S.A. Temperatures are all uncorrected, and percentages are all on weight basis.

EXAMPLE 1

A mixture of 0.214 g. of 7-aminodesacetoxycephalosporanic acid, 0.42 g. of sodium hydrogen carbonate, 5 ml. of water and 5 ml. of tetrahydrofuran is cooled to 5° C and, under stirring, 0.2 g. of diketene is added. The mixture is further stirred at room temperature for 30 minutes. The reaction mixture is washed with ethyl acetate and the water layer is taken, adjusted to pH 2 with 50% phosphoric acid and extracted three times with ethyl acetate. The ethyl acetate extracts are pooled, washed with a saturated aqueous solution to sodium chloride and dehydrated over magnesium sulfate. It is then concentrated and allowed to stand at room temperature. The resultant crystals are harvested by suction-filtration. The procedure gives 0.17 g. (50 %) of 7-acetoacetamido-3-methyl-3-cephem-4-carboxylic acid as crystals melting at 170°–173° C (decomp.).

IR($cm^{-1}$, KBr): 1760, 1730, 1665.

UV $\lambda$ max(E, in 5 % $NaHCO_3$): 261 nm (261).

NMR($\delta$, in $d_6$-DMSO): 2.02(3H, s, $CH_3CO$), 2.13(3H, s, 3-$CH_3$), 3.40(2H, s, $COCH_2CO$), 3.28 and 3.56(2H, ABq, J=18.0 Hz, 2-$CH_2$), 5.00(1H, d, J=4.8 Hz, 6-H), 5.55(1H, dd, J=48 & 8.0 Hz, 7-H), 8.94(1H, d, J=8.0 Hz, NH).

Elemental analysis: Calcd. for $C_{12}H_{14}N_2O_5S$: C, 48.32; H, 4.73; N, 9.39; Found: C, 47.88; H, 4.70; N, 8.94.

EXAMPLE 2

While a mixture of 2.72 g. of 7-aminocephalosporanic acid, 2.02 g. of triethylamine and 80 ml. of dichloromethane is cooled with ice and stirred, a solution of 1.0 g. of diketene in 10 ml. of dichloromethane is added dropwise.

The reaction mixture is stirred for 3 hours, after which time it is concentrated to dryness under reduced pressure. To the residue is added water and, then, ethyl acetate is superimposed. It is adjusted to pH 2 with 50 % phosphoric acid under vigorous stirring. The ethyl acetate layer is separated, washed with a saturated aqueous solution of sodium chloride and dehydrated over magnesium sulfate. It is then concentrated and chilled to −40° C. The resultant crystals are recovered by filtration and washed with ethyl acetate at −40° C. The procedure gives 7-acetoacetamido-3-acetoxymethyl-3-cephem-4-carboxylic acid as crystals melting at 148°–150° C (decomp.).

Yield 1.8 g. (70 %).

IR($cm^{-1}$, KBr): 1780, 1740, 1710, 1650.

UV $\lambda$ max (E in 5 % $NaHCO_3$): 260 nm (244).

NMR($\delta$, in $d_6$-DMSO): 2.02(3H, s, 3-$CH_3CO$), 2.12(3H, s, 7-$CH_3CO$), 3.41(2H, s, $COCH_2CO$), 3.41 & 3.65(2H, ABq, J=18 Hz, 2-$CH_2$), 4.68 & 4.99(2H, ABq, J=14 Hz, 3-$CH_2O$), 5.08(1H, d, J=5.0, 6-H), 5.66(1H, dd, J=5.0 & 8.0 Hz, 7-H), 8.98(1H, d, J=8.0 Hz, NH).

Elemental analysis: Calcd. for $C_{14}H_{16}N_2O_7S$: C, 47.19; H, 4.53; N, 7.86. Found C, 47.50; H, 4.63; N, 7.48.

EXAMPLE 3

A mixture of 0.356 g. of 7-acetoacetamido-3-acetoxymethyl-3-cephem-4-carboxylic acid, 0.84 g. of sodium hydrogen carbonate, 0.246 g. of 5-methyl-1,3,4-thiadiazol-2-thiol and 20 ml. of a phosphate buffer of pH 6.4 is heated at 60° C for 7.5 hours. After cooling, it is washed with ethyl acetate, adjusted to pH 2 with 50 % phosphoric acid, saturated with sodium chloride and extracted with ethyl acetate. The ethyl acetate layer is dried over magnesium sulfate and concentrated under reduced pressure, followed by cooling with ice. The resultant crystals are recovered by suction-filtration, washed with hexane and dried. The described procedure gives 7-acetoacetamido-3-(5-methyl-1,3,4-thiadiazol-2-yl)thiomethyl-3-cephem-4-carboxylic acid as crystals melting at 177°–180° C (decomp.). Yield 0.274 g. (64 %).

IR($cm^{-1}$, KBr): 1775, 1700, 1650.

UVλmax (E in 5 % $NaHCO_3$): 271 nm (288).

NMR (δ, in $d_6$-DMSO): 2.10(3H, s, $CH_3CO$), 2.62(3H, s, thiadiazole-$CH_3$), 3.37(2H, s, $COCH_2CO$), 3.50 & 3.74 (2H, ABq, J=18.0 Hz, 2-H), 4.15 & 4.46(2H, ABq, J=13.0 Hz, 3-$CH_2$), 5.02(1H, d, J=5.0 Hz, 6-H), 5.62(1H, dd, J=5.0 & 8.0 Hz, 7-H), 8.95(1H, d, J=8.0 Hz, NH).

Elemental analysis: Calcd. for $C_{15}H_{16}N_4O_5S_3$C, 42.04; H, 3.76; N, 13.08. Found C, 42.32; H, 3.98; N, 12.30.

EXAMPLE 4

While a mixture of 0.344 g. of 7-amino-3-(5-methyl-1,3,4-thiadiazol-2-yl)thiomethyl-3-cephem-4-carboxylic acid, 0.42 g. of sodium hydrogen carbonate, 5 ml. of water and 5 ml. of acetone is stirred under cooling at 5° C, 0.2 g. of diketene is added and the mixture is further stirred at room temperature for 30 minutes. The acetone is removed from the reaction mixture by distillation under reduced pressure and the residual is washed with ethyl acetate. The water layer is separated, adjusted to pH 2 with 50% phosphoric acid and extracted three times with ethyl acetate. The extracts are pooled, washed with a saturated aqueous solution of sodium chloride, dehydrated over magnesium sulfate, concentrated and allowed to stand under cooling with ice. With the addition of ether the resultant crystals are loosened and recovered by suction-filtration. The procedure gives 7-acetoacetamido-3(5-methyl-1,3,4-thiadiazol-2-yl)thiomethyl-3-cephem-4-carboxylic acid as crystals melting at 177°–180° C (decomp.). Yield 0.129 g. (30 %).

The IR and NMR spectra of this product are in good agreement with the corresponding spectra of the product according to Example 3.

EXAMPLE 5

A mixture of 0.35 g. of 7-acetoacetamido-3-acetoxymethyl-3-cephem-4-carboxylic acid, 0.84 g. of sodium hydrogen carbonate, 0.122 g. of 1-methyltetrazol-2-thiol and 20 ml. of a phosphate buffer of pH 6.4 is heated at 60° C for 16 hours. After cooling, the reaction mixture is washed with ethyl acetate, brought to pH 2 with 50 % phosphoric acid, saturated with sodium chloride and extracted five times with portions of ethyl acetate. The extracts are pooled, washed with a saturated aqueous solution of sodium chloride, dried over magnesium suflate and concentrated.

Ether is added to the concentrate and the mixture is allowed to stand. The crystals formed are loosened with the addition of ether and recovered by suction-filtration.

The described procedure gives 7-acetoacetamido-3-(1-methyltetrazol-5-yl)thiomethyl-3-cephem-4-carboxylic acid as crystals melting at 65°–70° C(decomp.). Yield 0.19 g. (46 %).

IR($cm^{-1}$, KBr): 1780.

UV(E in 5 % $NaHCO_3$): 266 nm (209).

NMR(δ in $d_6$-DMSO): 2.14(3H, s, $CH_3CO$), 3.41(2H, s, $COCH_2CO$), 3.67(2H, m, 2-$CH_2$), 3.92(3H, s, tetrazole-$CH_3$), 4.20 & 4.37(2H, ABq, J=14 Hz, 3-$CH_2$), 5.06(1H, d, J=5.0 Hz, 6-H), 5.65 (1H, dd, J=5.0 & 8.0, 7-H), 9.02 (1H, d, J=8.0 Hz, NH).

Elemental analysis: Calcd. for $C_{14}H_{16}N_6O_5S_2$: C, 40.78; H, 3.91; N, 20.38;. Found C, 41.10; H, 3.90; N, 17.63.

EXAMPLE 6

While a mixture of 0.328 g. of 7-amino-3-(1-methyltetrazol-5-yl)thiomethyl-3-cephem-4-carboxylic acid, 0.42 g. of sodium hydrogen carbonate, 5 ml. of water and 5 ml. of acetone is stirred under cooling at 5° C, 0.2 g. of diketene is added.

The mixture is further stirred at room temperature for 30 minutes, after which time the acetone is distilled off under reduced pressure. The residue is washed with ethyl acetate and the water layer is separated, brought to pH 2 with 50 % phosphoric acid, saturated with sodium chloride and extracted three times with ethyl acetate. The extracts are pooled, washed with a saturated aqueous solution of sodium chloride, dried over sodium sulfate, treated with activated carbon and concentrated. To the residue is added ethyl ether and the mixture is allowed to stand, whereupon 0.169 g. (41 %) of 7-acetoacetamido-3-(1-methyltetrazol-5-yl)thiomethyl-3-cephem-4-carboxylic acid is obtained as crystals melting at 65°–70° C (decomp.). The IR and NMR spectra of this product are in good agreement with the corresponding spectra of the product according to Example 5.

EXAMPLE 7

A mixture of 0.356 g. of 7-acetoacetamido-3-acetoxymethyl-3-cephem-4-carboxylic acid, 0.84 g. of sodium hydrogen carbonate, 0.156 g. of 6-methyl-1-oxidopyridazine-3-thiol and 20 ml. of a phosphate buffer of pH 6.4 is heated at 60° C for 7.5 hours. After cooling, the reaction mixture is washed with ethyl acetate, brought to pH 2 with 50 % phosphoric acid, saturated with sodium chloride and extracted with ethyl acetate. The ethyl acetate layer is dried over magnesium sulfate and concentrated under reduced pressure. The concentrate is allowed to stand under cooling with ice. The resultant crystals are loosened with the addition of ethyl ether, recovered by suction-filtration, washed with hexane and dried. The procedure gives 7-acetoacetamido-3-(6-methyl-1-oxidopyridazin-3-yl)thiomethyl-3-cephem-4-carboxylic acid as crystals melting at 85°–87° C (decomp.). Yield 0.18 g. (41 %).

IR($cm^{-1}$, KBr): 1775, 1710, 1525.

UV(E in 5 % $NaHCO_3$): 234 nm (394), 271 nm (436), 340 nm (111).

NMR(δ in d$_6$-DMSO): 2.10(3H, s, CH$_3$CO), 2.26(3H, s, pyridazine-CH$_3$), 3.37(2H, s, COCH$_2$CO), 3.46 & 3.75(2H, ABq, J=18.0 Hz, 2-CH$_2$), 4.02 & 4.29(2H, ABq, J=14.0 Hz, 3-CH$_2$), 5.04(1H, d, J=5.0 Hz, 6-H), 5.61(1H, dd, J=5.0 & 8.0 Hz, 7-H), 7.08 (d) & 7.68(d) (each 1H, d, J=8.61 Hz, pyridazine 4-H & 5-H), 8.96(1H, d, J=8.0 Hz, NH).

Elemental analysis: Calcd. for C$_{17}$H$_{18}$N$_4$O$_6$S$_2$: C, 46.58; H, 4.14; N, 12.78; Found: C, 46.42; H, 4.39; N, 11.37.

EXAMPLE 8

A mixture of 0.354 g. of 7-amino-3-(6-methyl-1-oxidopyridazin-3-yl)thiomethyl-3-cephem-4-carboxylic acid, 0.42 g. of sodium hydrogen carbonate, 5 ml. of water and 5 ml. of acetone is cooled to 5° C and under stirring, 0.2 g. of diketene is added. The mixture is further stirred at room temperature for 30 minutes. The acetone is distilled off under reduced pressure and the residue is washed with ethyl acetate. The water layer is separated, brought to pH 2 with 50 % phosphoric acid, saturated with sodium chloride and extracted three times with ethyl acetate. The extracts are pooled, washed with a saturated aqueous solution of sodium chloride, dried over magnesium sulfate, concentrated and allowed to stand under cooling with ice. The resultant crystals are loosened with the addition of ether and recovered by suction-filtration. The procedure gives 7-acetoacetamido-3-(6-methyl-1-oxidopyridazin-3-yl)thiomethyl-3-cephem-4-carboxylic acid as crystals melting at 85°–87° C(decomp.). Yield 0.13 g. (30 %).

The IR and NMR spectra of this product are in good agreement with the corresponding spectra of the product according to Example 7.

EXAMPLE 9

A mixture of 0.392 g. of 7-amino-3-(3-methoxy-1-oxidopyridazin-6-yl)thiomethyl-3-cephem-4-carboxylic acid, 0.42 of sodium hydrogen carbonate, 5 ml. of water and 5 ml. of acetone is cooled to 5° C and under stirring, 0.2 g. of diketene is added, followed by further stirring at room temperature for 30 minutes. The acetone is distilled off and the residue is adjusted to pH 7 with 50 % phosphoric acid, washed with ethyl acetate and developed on a column of polystyrene resin (Amberlite XAD-2) with 5 % aqueous alcohol. The desired fractions are pooled and freeze-dried. The above procedure gives sodium 7-acetoacetamido-3-(3-methoxy-1-oxidopyridazin-6-yl)thiomethyl-3-cephem-4-carboxylate trihydrate as a powder with a faint brownish tinge. Yield 0.152 g. (32 %).

IR(cm$^{-1}$, KBr): 1765.

NMR(δ in heavy water): 2.39(3H, s, CH$_2$CO), 3.53 & 3.83(2H, ABq, J=17 Hz, 2-CH$_2$), 3.94 & 4.15(2H, ABq, J=7 Hz, 3-CH$_2$), 4.04 (3H, s, OCH$_3$), 4.33(0.8H, s, COCH$_2$CO), 5.13(1H, d, J=5 Hz, 6-H), 5.71(1H, d, J=5 Hz, 7-H), 7.16 & 7.97 (each 1 H, each d, J=9 Hz, pyridazine 4-H and 5-H).

Elemental analysis: Calcd. for C$_{17}$H$_{17}$N$_4$O$_7$S$_2$Na.3-H$_2$O: C, 39.48; H, 4.37; N, 10.56; Found: C, 38.85; H, 4.03; N, 10.21.

EXAMPLE 10

A mixture of 0.356 g. of 7-acetoacetamido-3-acetoxymethyl-3-cephem-4-carboxylic acid, 0.84 g. of sodium hydrogen carbonate, 0.237 g. of 3-methoxy-1-oxidopyridazine-6-thiol and 20 ml. of a phosphate buffer of pH 6.4 is heated at 60° C for 13.5 hours. After cooling, the reaction mixture is washed with ethyl acetate and the water layer is separated, brought to pH 2 with 50 % phosphoric acid, saturated with sodium chloride and extracted with butanol. The extract is dried over sodium sulfate and concentrated to dryness under reduced pressure. The residue is dissolved in a solution of 0.84 g. sodium hydrogen carbonate in 20 ml. water and the solution is developed on a column of polystyrene resin (Amberlite XAD-2) with 5 % aqueous alcohol. The desired fractions are pooled and freeze-dried.

The described procedure gives sodium 7-acetoacetamido-3-(3-methoxy-1-oxidopyridazin-6-yl)thiomethyl-3-cephem-4-carboxylate trihydrate as a powdery product. Yield 0.048 g. (9 %). The IR and NMR spectra of this product are in good agreement with the corresponding spectra of the product according to Example 9.

EXAMPLE 11

A mixture of 0.356 g. of 7-acetoacetamido-3-acetoxymethyl-3-cephem-4-carboxylic acid, 0.84 g. of sodium hydrogen carbonate, 0.179 g. of 3-chloro-1-oxidopyridazine-6-thiol and 20 ml. of a phosphate buffer of pH 6.4 is heated at 50° C for 24 hours. After cooling, the insolubles are filtered off and the filtrate is brought to pH 1.5 with 50 % phosphoric acid and extracted with several portion of ethyl acetate. The extracts are pooled, dried over anhydrous sodium sulfate and concentrated to dryness. The residue is dissolved in 5 ml. of a saturated solution of sodium hydrogen carbonate and developed on a column of polystyrene resin (Amberlite XAD-2) with 5 % aqueous alcohol. The desired fractions are pooled and freeze-dried.

The procedure gives 0.118 g. (23.7 %) of sodium 7-acetoacetamido-3-(3-chloro-1-oxidopyridazin-6-yl)thiomethyl3-cephem-4-carboxylate monohydrate as a powdery product.

UV(E in water): 233 nm (351), 280 nm (375), 345 nm (61).

NMR(δ in heavy water): 2.38(3H, s, CH$_3$CO), 3.53 & 3.83(2H, ABq, J=18 Hz, 2-CH$_2$), 4.13 & 4.38(2H, ABq, J=14 Hz, 3-CH$_2$S), 5.18(1H, d, J=4.5 Hz, 6-H), 5.72(1H, d, J=4.5, 7-H), 7.65 & 8.12(each 1H, each d, J=9.0 Hz, pyridazine 4-H & 5-H).

Elemental analysis: Calcd. for C$_{16}$H$_{14}$N$_4$O$_6$S$_2$Cl-Na.H$_2$O C, 38.52; H, 3.23; N, 11.23. Found: C, 38.31; H, 3.12; N, 10.99.

EXAMPLE 12

A mixture of 0.178 g. of 7-acetoacetamido-3-acetoxymethyl-3-cephem-4-carboxylic acid, 0.82 g. of 1-oxidopyridine-2-thiol sodium and 20 ml. of a phosphate buffer of pH 6.4 is heated at 60° C for 7 hours. After cooling, 0.84 g. of sodium hydrogen carbonate is added and the mixture is developed on a column of polystyrene resin(Amberlite XAD-2) with 5 % aqueous alcohol. The desired fractions are collected and freeze-dried to recover 0.176 g. (36 %) of sodium 7-acetoacetamido-3-(1-oxidopyridin-2-yl)thiomethyl-3-cephem-4-carboxylate 2.5 hydrate.

IR(cm$^{-1}$, KBr): 1755, 1600.

UV(E in 5 % NaHCO$_3$): 266 nm (209).

NMR(δ in heavy water): 2.39(3H, s, CH$_3$CO), 3.51 & 3.81 (2H, ABq, J=18.0 Hz, 2-CH$_2$), 4.05 & 4.38(2H, Abq, J=13.0 Hz, 3-CH$_2$), 5.17(1H, d, J=4.0 Hz, 6-H), 5.72(1H, d, J=4.0 Hz, 7-H), 7.3–7.8 & 8.36(4H, m & d, pyridine ring H).

Elemental analysis: Calcd. for $C_{17}H_{16}N_3O_6S_2Na \cdot 2.5-H_2O$: C, 41.63; H, 4.32; N, 8.57. Found: C, 41.46; H, 3.77; N, 7.85.

EXAMPLE 13

A mixture of 0.178 g. of 7-acetoacetamido-3-acetoxymethyl-3-cephem-4-carboxylic acid, 0.42 g. of sodium hydrogen carbonate, 0.55 g. of 4-H-1,2,4-triazole-3-thiol and 10 ml. of a phosphate buffer of pH 6.4 is heated at 55° to 60° C for 16 hours. After cooling, the reaction mixture is shaken with ethyl acetate and the water layer is taken, adjusted to pH 2 with 50 % phosphoric acid and saturated with sodium chloride. It is then extracted four times with a 1:1 mixture of ethyl acetate and tetrahydrofuran. The extracts are pooled, washed with a saturated aqueous solution of sodium chloride and dehydrated over magnesium sulfate. The solvent is distilled off and with the addition of ether to the residue, the internal wall of the vessel is rubbed. The procedure gives 0.92 g. (46 %) of 7-acetoacetamido-3-(4-H-1,2,4-triazol-3-yl)thiomethyl-3-cephem-4-carboxylic acid as crystals melting at 87° C(decomp.).

IR(cm$^{-1}$, KBr): 1765, 1700, 1650.
UV(E in 5 % NaHCO$_3$): 268 nm (234).
NMR($\delta$ in d$_6$-DMSO): 2.14(3H, s, CH$_3$CO), 3.40(2H, s, COCH$_2$CO), 3.25 & 3.52(2H, ABq, J=18.0 Hz, 2-CH$_2$), 4.02 & 4.28(2H, ABq, J=13.0 Hz, 3-CH$_2$), 5.04(1H, d, J=5.0 Hz, 6-H), 5.62(1H, dd, J=5.0 & 8.0 Hz, 7-H), 8.35(1H, s, triazole 5-H), 8.98(1H, d, J=8.0 Hz, NH).

EXAMPLE 14

A mixture of 0.178 g. of 7-acetoacetamido-3-acetoxymethyl-3-cephem-4-carboxylic acid, 0.42 g. of sodium hydrogen carbonate, 0.64 g. of 5-methyl-1,3,4-oxadiazole-2-thiol and 10 ml. of a phosphate buffer of pH 6.4 is heated at 55°–60° C for 16 hours. After cooling, the reaction mixture is shaken with ethyl acetate and the water layer is taken, adjusted to pH 2 with 50 % phosphoric acid and extracted three times with ethyl acetate. The extracts are pooled, washed with water and dehydrated over sodium sulfate. Then, the solvent is distilled off and ether is added to the residue, whereupon 0.10 g. (48 %) of 7-acetoacetamido-3-(5-methyl-1,3,4-oxadiazol-2-yl)thiomethyl-3-cephem-4-carboxylic acid is obtained as crystals melting at 80°–85° C(decomp.).

IR(cm$^{-1}$, KBr): 1780, 1715.
UV(E in 5 % NaHCO$_3$): 264 nm (260).
NMR($\delta$ in d$_6$-DMSO): 2.12(3H, s, CH$_3$CO), 2.43(3H, s, oxadiazole-CH$_3$), 3.39(2H, s, COCH$_2$CO), 3.51 & 3.77(2H, ABq, J=18.0 Hz, 2-CH$_2$), 4.11 & 4.35(2H, ABq, J=14.0 Hz, 3-CH$_2$), 5.05(1H, d, J=4.0 Hz, 6-H), 5.65(1H, dd, J=4.0 & 8.0 Hz, 7-H), 8.99(1H, d, J=8.0 Hz, NH).

What is claimed is:

1. A compound of the formula:

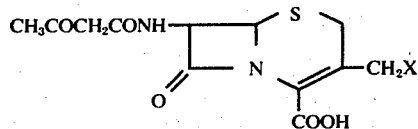

wherein X is a —SR group, R being a substituted or unsubstituted five-or-six-membered heterocyclic ring which contains at least one nitrogen atom that may be in the oxide form and which may contain in addition to said at least one nitrogen atom, one oxygen or sulfur atom, and the substituted ring being substituted by one or more substituents selected from the group consisting of alkyl, alkoxy, halogen, carboxyalkyl, carbamoylalkyl, alkoxycarbonylalkyl, N-alkylcarbamoylalkyl, alkylthioalkyl, N-alkylaminoalkyl, morpholinoalkyl, amino, sulfoalkylamino, acetylamino, propionylamino, N-alkylaminomethylcarbonylamino, mercapto, alkylthio, hydroxyalkylthio, alkylcarbonyloxyalkylthio, carboxyalkylthio, alkoxycarbonylalkylthio, N-alkylaminocarbonylalkylthio, morpholinocarbonylalkylthio, N-alkylaminoalkylthio, sulfoalkylthio, alkoxyalkylthio and morpholino, wherein said alkyl and alkoxyl groups are lower alkyl and lower alkoxyl groups respectively, or a pharmaceutically acceptable salt or ester thereof.

2. A compound according to claim 1, wherein the five- or six-membered ring is selected from the group consisting of pyrazolyl, imidazolyl, thiazolyl, thiadiazolyl, oxadiazolyl, triazolyl, tetrazolyl, pyridinyl, pyrimidinyl and pyridazinyl.

3. A compound according to claim 1, wherein the five- or six-membered ring is substituted with one or more substituents selected from the group consisting of lower alkyl, lower alkoxy, carbamoylloweralkyl, amino, acetylamino, propionylamino, mercapto, lower alkylthio, loweralkoxycarbonylloweralkylthio, morpholino and halogen.

4. A compound according to claim 1, wherein the five- or six-membered ring is thiadiazolyl.

5. 7-Acetoacetamido-3-(5-methyl-1,3,4-thiadiazol-2-yl)thiomethyl-3-cephem-4-carboxylic acid.

6. A compound according to claim 1, wherein the five- or six-membered ring is tetrazolyl.

7. 7-Acetoacetamido-3-(1-methyltetrazol-5-yl)thiomethyl-3-cephem-4-carboxylic acid.

8. A compound according to claim 1, wherein the five- or six-membered ring is pyridazinyl.

9. 7-Acetoacetamido-3-(6-methyl-1-oxidopyridazin-3-yl)thiomethyl-3-cephem-4-carboxylic acid.

10. 7-Acetoacetamido-3-(3-methoxy-1-oxidopyridazin-6-yl)thiomethyl-3-cephem-4-carboxylic acid.

11. 7-Acetoacetamido-3-(3-chloro-1-oxidopyridazin-6-yl)thiomethyl-3-cephem-4-carboxylic acid.

12. A compound according to claim 1, wherein the five- or six-membered ring is pyridinyl.

13. 7-Acetoacetamido-3-(1-oxidopyridin-2-yl)thiomethyl-3-cephem-4-carboxylic acid.

14. A compound according to claim 1, wherein the five- or six-membered ring is triazolyl.

15. 7-Acetoacetamido-3-(4-H-1,2,4-triazol-3-yl)thiomethyl-3-cephem-4-carboxylic acid.

16. A compound according to claim 1, wherein the five- or six-membered ring is oxadiazolyl.

17. 7-Acetoacetamido-3-(5-methyl-1,3,4-oxadiazol-2-yl)thiomethyl-3-cephem-4-carboxylic acid.

18. A compound according to claim 1, wherein R is a substituted or unsubstituted five- or six-membered heterocyclic ring selected from the group consisting of pyrazolyl, imidazolyl, thiazolyl, thiadiazolyl, oxadiazolyl, triazolyl, tetrazolyl, pyridinyl, pyrimidinyl and pyridazinyl, the substituted ring being substituted with one or more substituents selected from the group consisting of lower alkyl, lower alkoxyl, carbamoylloweralkyl, amino acetylamino, propionylamino, mercapto, lower alkylthio, lower alkoxycarbonylloweralkylthio, morpholino and halogen.

* * * * *